US011327080B2

(12) United States Patent
Lannfelt et al.

(10) Patent No.: US 11,327,080 B2
(45) Date of Patent: May 10, 2022

(54) METHOD FOR TREATMENT OF TRAUMATIC BRAIN INJURY TARGETING AGGREGATED PEPTIDES

(71) Applicant: BioArctic AB, Stockholm (SE)

(72) Inventors: Lars Lannfelt, Stockholm (SE); Hans Basun, Stockholm (SE); Erik Rollman Waara, Stockholm (SE)

(73) Assignee: BioArctic Neruoscience AB, Stockholm (SE)

( * ) Notice: Subject to any disclaimer, the term of this patent is extended or adjusted under 35 U.S.C. 154(b) by 0 days.

(21) Appl. No.: 15/746,283

(22) PCT Filed: Jul. 20, 2016

(86) PCT No.: PCT/IB2016/054318
§ 371 (c)(1),
(2) Date: Jan. 19, 2018

(87) PCT Pub. No.: WO2017/013599
PCT Pub. Date: Jan. 26, 2017

(65) Prior Publication Data

US 2018/0209994 A1 Jul. 26, 2018

Related U.S. Application Data

(60) Provisional application No. 62/288,813, filed on Jan. 29, 2016, provisional application No. 62/195,183, filed on Jul. 21, 2015.

(51) Int. Cl.
*G01N 33/68* (2006.01)
*A61K 39/00* (2006.01)
*C07K 16/18* (2006.01)

(52) U.S. Cl.
CPC ......... *G01N 33/6896* (2013.01); *C07K 16/18* (2013.01); *A61K 2039/505* (2013.01); *G01N 2333/4709* (2013.01); *G01N 2800/2821* (2013.01); *G01N 2800/2871* (2013.01); *G01N 2800/50* (2013.01); *G01N 2800/52* (2013.01); *G01N 2800/7047* (2013.01)

(58) Field of Classification Search
CPC ....... G01N 33/6896; G01N 2333/4709; G01N 2800/2821; G01N 2800/2871; G01N 2800/50; G01N 2800/52; G01N 2800/7047; C07K 16/18; A61K 2039/505; A61P 9/00; A61P 25/00; A61P 25/28
See application file for complete search history.

(56) References Cited

U.S. PATENT DOCUMENTS 8,025,878 B2 9/2011 Gellerfors et al.
8,106,164 B2 1/2012 Gellerfors et al.
8,614,299 B2 12/2013 Baurin et al.
9,573,994 B2 2/2017 Nerelius et al.
2009/0074775 A1 3/2009 Holtzman et al.
2015/0004169 A1 1/2015 Kayed
2015/0126390 A1 5/2015 Diamond et al.

FOREIGN PATENT DOCUMENTS

CN 103228674 A 7/2013
WO WO-2001/062801 A2 8/2001
WO 02/03911 A2 1/2002
WO 2005/123775 A1 12/2005
WO 2006/069081 A2 6/2006
WO 2007/108756 A1 9/2007
WO 2011/001366 A1 1/2011
WO WO-2011/026031 A1 3/2011
WO 2011/104696 A1 9/2011
WO 2013/168174 A1 11/2013
WO WO 2014/089500 * 6/2014 ........... A61K 39/395
WO 2015/035190 A1 3/2015

OTHER PUBLICATIONS

Tokuraku et al., PLoS ONE, 4(12):e8492, 2009.*

Faden et al., Chronic Neurodegeneration After Tramatic Brain Injury: Alzheimer Disease, Chronic Traumatic Encephalopathy, or Persistent Neuroinflammation?, Neurotherapeutics 12:143-150 (online Nov. 25, 2014).

Boutajangout et al., Passive immunization targeting pathological phospho-tau protein in a mouse model reduces functional decline and clears tau aggregates from the brain, Journal of Neurochemistry, 118:658-667 (2011).

Hori et al., Role of Apolipoprotein E in B-Amyloidogenesis Isoform-Specific Effects on Protofibril To Fibril Conversion of A B in vitro and Brain A B Deposition in Vivo, Journal of Biological Biochemistry, vol. 290, No. 24, pp. 15163-15174 (Jun. 12, 2015).

Lannfelt et al., Perspectives on future Alzheimer therapies: amyloid-B protofibrils—a new target for immunotherapy with BAN2401 in Alzeimer's disease, Alzeimer's Research & Therapy, 6:16 (pp. 1-8) (2014).

(Continued)

*Primary Examiner* — Kimberly Ballard
*Assistant Examiner* — Stacey N MacFarlane
(74) *Attorney, Agent, or Firm* — Marshall, Gerstein & Borun LLP

(57) ABSTRACT

A method of preventing, alleviating or treating traumatic brain injury in an individual comprises administering to the individual a therapeutically effective and physiologically acceptable amount of an agent capable of reducing the amount of one or more aggregated forms of one or more peptides in the brain. An agent capable of reducing the amount of one or more aggregated forms of one or more peptides in the brain is suitable for use in preventing, alleviating or treating traumatic brain injury. A method for predication of the risk of an individual for complications after a traumatic brain injury comprises detecting one or more aggregated forms of one or more peptides prone to aggregate as a result of a traumatic brain injury event, in the brain of the individual, wherein an increased level of such aggregates in the brain indicates an increased risk for complications.

11 Claims, 2 Drawing Sheets

Specification includes a Sequence Listing.

(56) References Cited

OTHER PUBLICATIONS

Balakrishnan et al., Impact of amyloid B aggregate maturation on antibody treatment in APP23 mice, Acta Neuropathologica Communications 3:41 (pp. 1-17) (Jul. 4, 2015).
Jullienne et al., Juvenile traumatic brain injury induces long-term perivascular matrix changes alongside amyloid-beta accumulation, Journal of Cerebral Blood Flow & Metabolism, 34:1637-1645 (Oct. 1, 2014).
Magnoni et al., New Perspectives on Amyloid-B Dynamics After Acute Brain Injury, Arch Neurol, vol. 67, No. 9, pp. 1068-1072 (Sep. 2010).
Tucker et al., The Murine Version of BAN2401 (mAb158) Selectively Reduces Amyloid-B Protofibrils in Brain and Cerebrospinal Fluid of tg-ArcSwe Mice, Journal of Alzeimer's Disease, 43:575-588 (Jan. 1, 2015).
Bard et al., Peripherally administered antibodies against amyloid b-peptide enter the central nervous system and reduce pathology in a mouse model of Alzheimer disease, Nature Medicine, vol. 6, No. 8, pp. 916-919 (Aug. 2000).
Washington et al., Experimental Traumatic Brain Injury Induces Rapid Aggregation and Oligomerization of Amyloid-Beta in an Alzheimer's Disease Mouse Model, Journal of Neurotrauma, 31:125-134 (Jan. 1, 2014).
Finder et al., Amyloid-B Aggregation, Neurodegenerative Diseases, 4:13-27 (2007).
Levin et al., Vegetative State After Closed-Head Injury A Traumatic Coma Data Bank Report, Arch Neurol, vol. 48, pp. 580-585 (1991).
Tagliaferri et al., A systematic review of brain injury epidemiology in Europe, Act Neurochir, 148:255-268 (2006).
Ikonomovic et al., Alzeimer's pathology in human temporal cortex surgically excised after severe brain injury, Experimental Neurology, 190:192-203 (2004).
Roberts et al., Amyloid protein deposition in the brain after severe head injury: implications for the pathogenesis of Alzheimer's disease, Neurol. Neurosurg. Psych., 57:419-425 (1994).
Walsh et al., Amyloid Beta-Protein Fibrillogenesis, The Journal of Biological Chemistry, vol. 274, No. 36, pp. 25945-25952 (1999).
Walsh et al., Amyloid Beta-Protein Fibrillogenesis, The Journal of Biological Chemistry, vol. 272, No. 35, pp. 22364-22372 (1997).
Alzforum Ban 2401, https://www.alzforum.org/therapeutics/ban2401, downloaded Jun. 15, 2020.

* cited by examiner

METHOD FOR TREATMENT OF TRAUMATIC BRAIN INJURY TARGETING AGGREGATED PEPTIDES

SEQUENCE LISTING

The Sequence Listing submitted herewith, entitled "Sequence-Listing-202309-PCT.txt", created Jan. 19, 2018 and having a size of 652 bytes, is incorporated herein by reference.

FIELD OF THE INVENTION

This invention is directed to prevention, alleviation, treatment and diagnosis of traumatic brain injury.

BACKGROUND OF THE INVENTION

Acute brain injury, ischemic or hemorrhagic, encompasses a group of common disorders, comprising, e.g., traumatic brain injury (TBI), hypoxi and stroke, leading to severe pathological consequences. TBI is the most common cause of death and disability in persons between 15 and 30 years of age. The most severe injuries can result in prolonged disorders of unconsciousness. From 10 to 15% of patients with severe TBI are discharged from acute care in a vegetative state (Levin et al., 1991 Arch Neurol; 48:580-5). Twenty three European reports with findings from national studies from Denmark, Sweden, Finland, Portugal, Germany, and from regions within Norway, Sweden, Italy, Switzerland, Spain, Denmark, Ireland, the U.K. and France reported an aggregate hospitalized plus fatal TBI incidence rate of about 235 per 100,000 (Tagliaferri et al., Acta Neurochir (Wien). 2006; 148:255-68). In the study, an average mortality rate of about 15 per 100,000 was reported.

The incomplete understanding of the pathogenesis of traumatic brain injury does not permit a construction of a rigorous temporal sequence of events. The most frequently proposed cellular mechanism is diffuse axonal injury, which is associated with alterations in several physiological processes. Altered proteostasis is among the most obvious, because different protein aggregation is often seen at the histopathological level. Interestingly, there is an overlap between the pathways of idiopathic neurodegeneration and neurodegeneration due to the injury, since identical protein aggregates in both conditions.

Amyloid-beta (Aβ), in the form of Aβ plaques and intra-axonal Aβ deposits, have been found in one-third of patients with fatal TBI who did not have symptoms of preexisting clinical dementia or cognitive deficits (Roberts et al., J Neurol Neurosurg Psychiatry. 1994; 57:419-25). As early as 2 hours after severe brain injury, increased levels of soluble Aβ peptide and deposition of amyloid plaques are evident in the brains of 30% of survivors, regardless of their age (Ikonomovic et al., Exp Neurol 2004; 190:192-203).

In intensive care units, intra-cerebral microdialysis is routinely used to monitor patients after neurosurgical procedures. Brain microdialysis has among other applications been used clinically to detect early signs of metabolic deterioration that may provide early warning signs of secondary insults after acute brain injury. Microdialysis catheters have at the same time been used to measure levels of Aβ. Brain interstitial fluid levels of Aβ increased when the patients' neurological status improved. Aβ levels remained stable when the patients were clinically stable (Magnoni et al., Arch Neurol 2010; 67:1068-73). It also appeared that the Aβ concentrations declined when the patients' neurological status worsened. The interstitial fluid levels of Aβ in the brain were also related to metabolic changes: low interstitial fluid levels of Aβ were related to high cerebral lactate-pyruvate ratios and low cerebral glucose levels.

Like several other proteins, Aβ has the ability to self-associate and can form different assemblies ranging from dimers to oligomers of various sizes, including protofibrils, which are larger soluble oligomers, to insoluble aggregates of fibrils. The formation and accumulation of Aβ fibrils in amyloid plaques in the brain was previously linked to neurodegenerative disease, in particular Alzheimer's disease. However, recent data suggest a more important role for the non-fibrillary and soluble, toxic species of Aβ, as biochemical analyses of brains have indicated that the concentrations of non-fibrillary forms of Aβ correlate well with synaptic loss and presence of dementia.

Therefore, considerable efforts have been focused on the development of therapies for Alzheimer's disease, based on therapeutic agents targeting one or more of the Aβ species, including soluble as well as insoluble species. In most cases, the proposed therapeutic agents are less specific and target monomers and/or various soluble aggregates, as well as insoluble aggregate forms. Accordingly, a broad range of antibodies targeting various Aβ forms with various degrees of specificity have been disclosed in the literature over the years.

WO 02/03911 describes the Aβ protofibril to be of special importance in the development of certain neurodegenerative diseases, in particular Alzheimer's disease, and antibodies with high affinity and selectivity for Aβ protofibrils were produced as disclosed in WO 05/123775 and WO 07/108756. Such an antibody is now in clinical trials for treatment of Alzheimer's disease.

SUMMARY OF THE INVENTION

In one embodiment, the invention is directed to a method of preventing, alleviating or treating traumatic brain injury in an individual. The method comprises administering to the individual a therapeutically effective and physiologically acceptable amount of an agent capable of reducing the amount of one or more aggregated forms of one or more peptides in the brain.

In another embodiment, the invention is directed to an agent capable of reducing the amount of one or more aggregated forms of one or more peptides in the brain, for use in preventing, alleviating or treating traumatic brain injury.

In another embodiment, the invention is directed to a method for predication of the risk of an individual for complications after a traumatic brain injury, comprising detecting one or more aggregated forms of one or more peptides prone to aggregate as a result of a traumatic brain injury event, in the brain of the individual, wherein an increased level of such aggregates in the brain indicates an increased risk for complications.

Further embodiments, aspects and advantages of the invention will be evident in view of the Detailed Description.

BRIEF DESCRIPTION OF THE DRAWINGS

FIG. 1A shows protofibril Aβ levels in patient samples detected with the mAb158 sandwich ELISA. Each bar represents a mean value and standard deviation (SD) from two ELISA experiments performed on two different occasions. FIG. 1B shows oligomer Aβ levels in patient samples detected with the mAb82E1 sandwich ELISA. Each bar represents a mean value and SD from two ELISA experiments performed on two different occasions. The absence of a bar indicates that the value was below the assay limit of detection.

FIG. 2A shows total monomeric Aβ x-40 and x-42 levels (N-terminal truncated and full-length monomers, wherein at least amino acid 40 and 42, respectively, is present) detected by mid-region mAb4G8. Each bar represents a mean and SD from two ELISA experiments performed on two different occasions. Six of the values from the Alzheimer's Disease (AD) sample panel are out-of scale and are instead shown above each bar as even thousands of pg per mg total protein. FIG. 2B shows full-length monomeric Aβ 1-40 and 1-42 levels detected by N-terminal mAb6E10. Each bar represents a mean from one ELISA experiment with SD showing variation between duplicate ELISA wells. Four of the values from the AD sample panel are out-of scale and are instead shown above each bar as even thousands of pg per mg total protein. The levels of Aβ 38 (Aβ peptides wherein at least amino acids x-38 are present) were below detection in the majority of samples (data not shown).

DETAILED DESCRIPTION

Figure 1A:
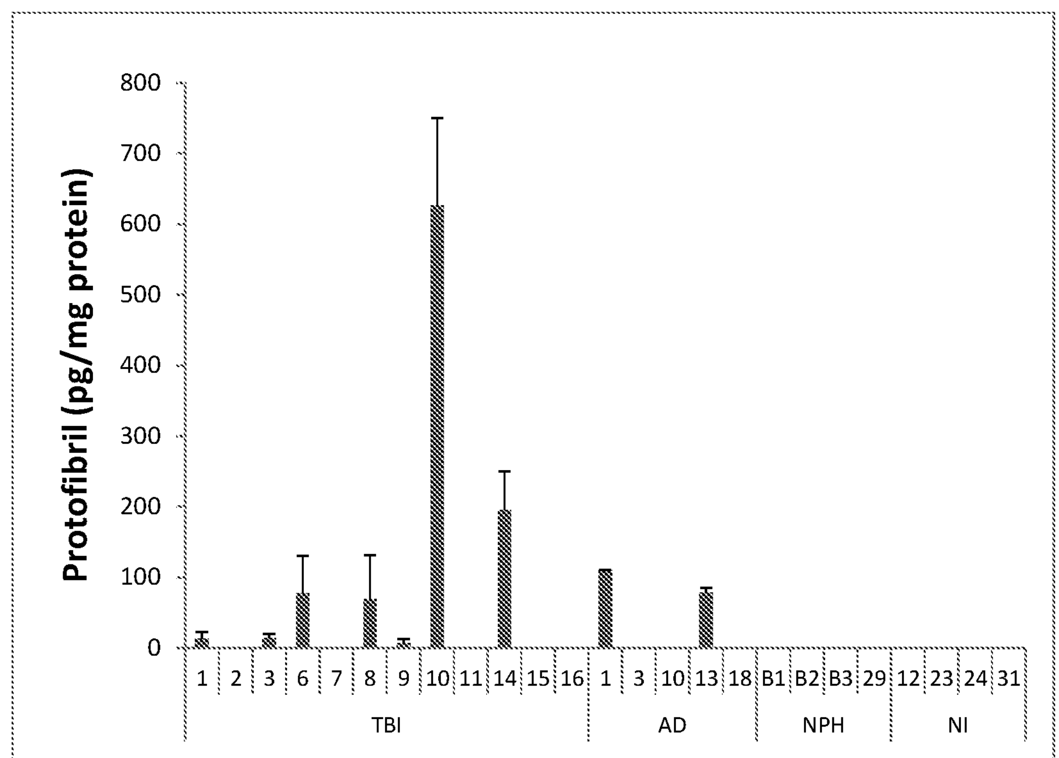
FIGS. 1A and 1B show protofibril and oligomer Aβ binding as described in the Example.
Figure 1B:
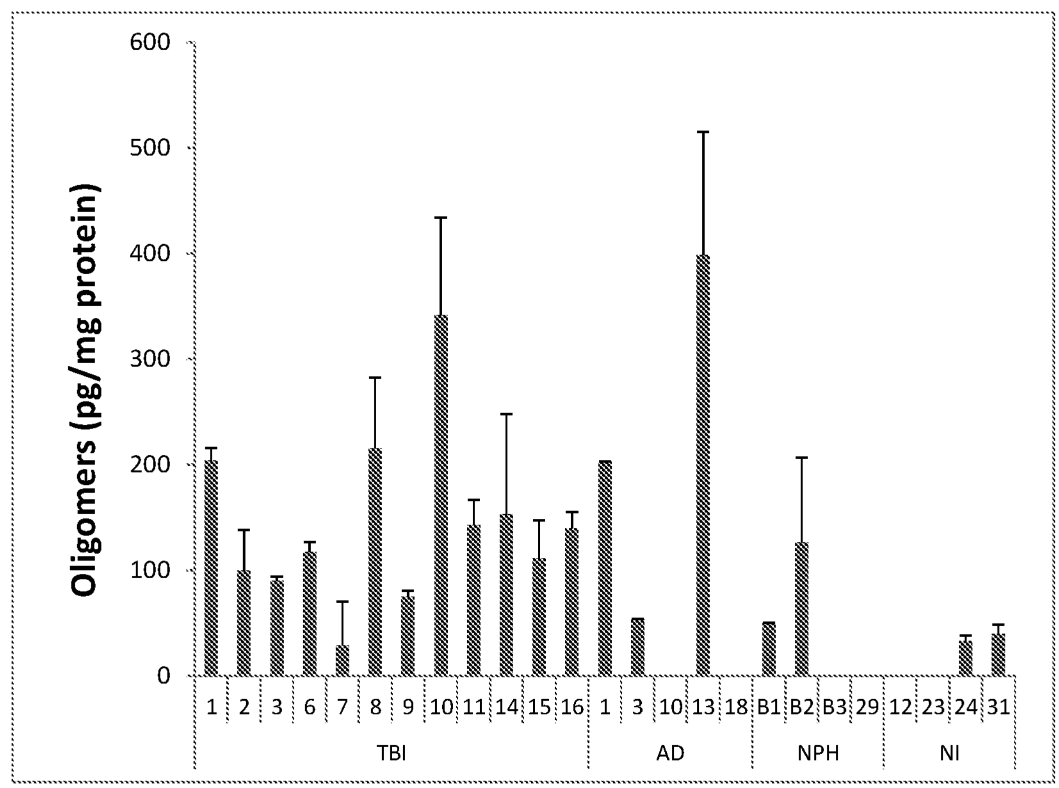
Figure 2A:
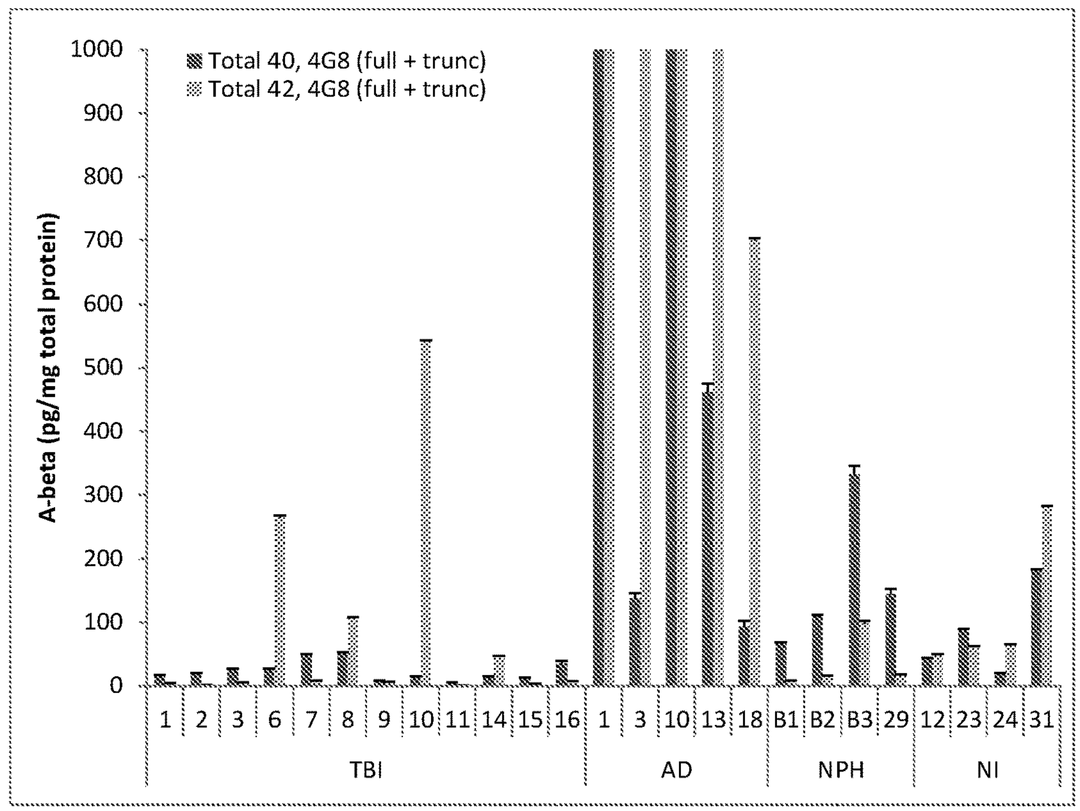
FIGS. 2A and 2B show monomeric Aβ 40 and 42 binding as described in the Example.
Figure 2B:
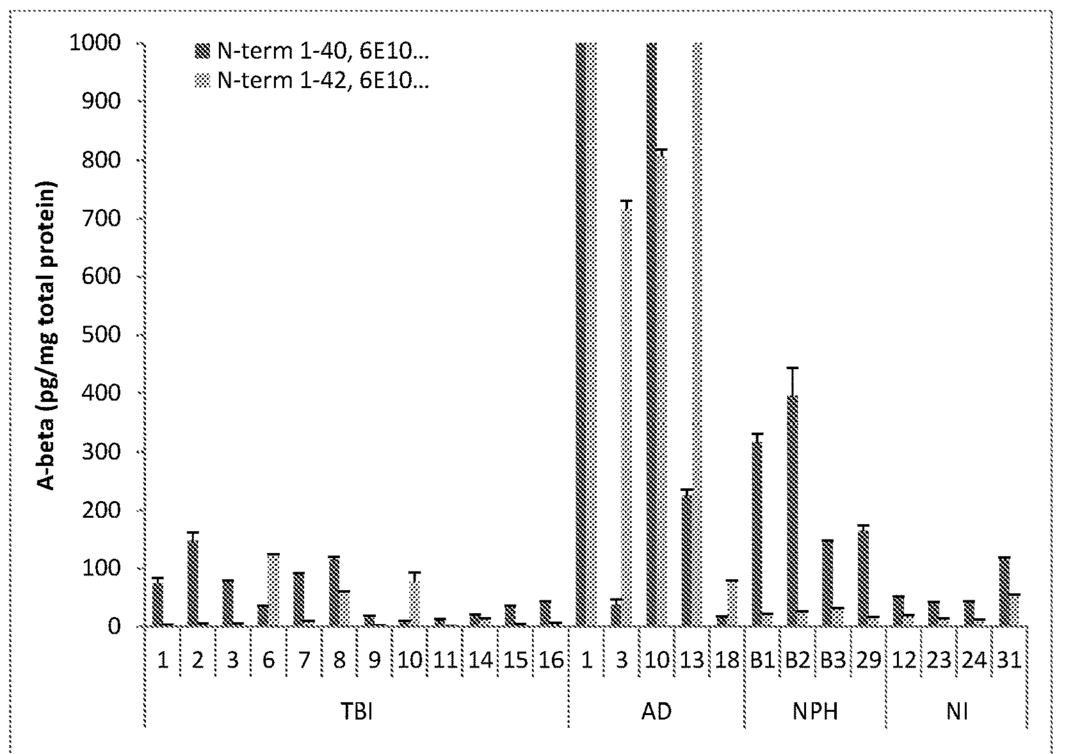

Certain peptides in the brain have been identified as being prone to aggregate as a result of an acute brain injury. The aggregates that are formed, in particular toxic aggregates, provide a severe contribution to the damages to vital functions that are most often the result already in the acute phase. Methods and means are provided according to the invention for acute treatments and diagnosis, targeting precursors of these peptides, the peptides themselves, or aggregated forms thereof. Accordingly, several possibilities for therapy are available in order to reach the goal that is to eliminate or substantially reduce the amount of aggregates in the brain. In particular, embodiments, the methods and agents of the invention target amyloid-β (Aβ), α-synuclein and/or tau peptide and/or tau peptide derivatives, e.g. P-tau, and/or oligomeric forms of these peptides, such as protofibrils. Within the present disclosure, protofibrils refers to larger soluble oligomers. In specific embodiments, the protofibrils have an apparent molecular weight greater than 100 kDa. In more specific embodiments, the protofibrils have an apparent molecular weight greater than 100 kDa, and a curvilinear structure of 4-11 nm in diameter and less than 200 nm in length. Such protofibrils are described, for example, by Walsh et al, The Journal of Biological Chemistry, 272(35): 22364-22372 (1997), and Walsh et al, The Journal of Biological Chemistry, 274(36):25945-25952 (1999), both of which are incorporated herein by reference. In more specific embodiments, the methods and agents of the invention target the neurotoxic Aβ protofibrils. According to specific embodiments of the invention, prevention, alleviation, treatment and/or diagnosis of a traumatic brain injury is achieved by the use of antibodies against one or more species comprising such a peptide. In the present description, the term peptide(s) will be used while the scientific literature sometimes refers to them as protein(s).

According to the present invention, elimination or at least substantial reduction of aggregated forms of certain target peptides in the brain provides efficient therapy in a new medical indication, i.e., situations with an acute brain injury event. These target peptides in the brain are characterized by the formation of aggregates in response to an acute brain injury event. The group of peptides prone to aggregate, under these conditions, comprises amyloid peptides, in particular the Aβ peptide, α-synuclein and tau peptide. The invention will in the following be illustrated mainly by exemplification with an amyloid peptide, Aβ, one member from the group of peptides in the brain, prone to aggregate as a result of an acute brain injury event. However, the invention covers as well, other peptides prone to aggregate in a similar way, as a result of an acute brain injury event. The elimination or substantial reduction can be obtained in several different ways. Normally the peptide, e.g., Aβ, is part of a receptor expressed in vivo, e.g. the Amyloid Precursor Protein (APP), and is cleaved off with one or more enzymes. By effecting the production of Aβ, e.g., on the expression level or cleavage level of APP, the number of species that can undergo an aggregation reaction is reduced. Substances affecting these processes in the Aβ system are, e.g., α-secretase agonists, antagonists of β-secretase and γ-secretase. Reduction of Aβ peptide can also be achieved by stimulation of Aβ degrading enzymes, e.g., by insulin degrading enzyme (IDE), neprilysin and others.

Elimination or at least substantial reduction of aggregated forms of the peptides may also be achieved by substances inhibiting the aggregation process as such, i.e., making the peptide monomers less prone to aggregate at all or preventing low molecular weight aggregates to undergo further aggregation to the most likely larger toxic aggregates, in particular, the protofibrils, i.e., larger soluble oligomers. For example, this can be achieved by administering substances which bind to peptide monomers and/or the low molecular weight aggregates, preventing them from further aggregation. Elimination of aggregated forms can of course also be achieved by administering substances targeting one or more of such aggregated forms for elimination of the species from the system, e.g., by disintegration to amino acids and/or monomers or less toxic small aggregates. Of special interest is the use of antibodies designed to have high affinity for aggregated forms of Aβ, α-synuclein or tau peptide. In specific embodiments, the invention is directed to the use of antibodies designed to have high affinity for, in particular, the protofibrils, for example, protofibrils of Aβ, α-synuclein or tau peptide. According to a further aspect of the invention, the toxic oligomeric or protofibril forms can be eliminated by an antibody-mediated uptake by microglial cells. According to a further aspect of the invention, the toxicity of oligomeric forms, in particular, protofibrils, is reduced, e.g., by administration of substances destroying or blocking toxic sites on the protofibrils.

Accordingly, in one embodiment, methods of preventing, alleviating and/or treating traumatic brain injury comprise administering to an individual an effective amount of an agent for reducing the amount of one or more aggregated forms of the peptide(s), e.g., with antibodies specific for peptides prone to aggregation after an acute brain injury, or their aggregated forms. In a specific embodiment of the invention, antibodies against Aβ or aggregated forms of Aβ are used to reduce the amount of one or more aggregated forms of the peptide(s), in order to enhance arousal and/or behavioral responsiveness, to avoid prolonged disorders of unconsciousness, and/or to alter the pace of recovery or improve the functional outcome. The goal is to regain wakefulness, conscious awareness, avoid a vegetative state and/or improve cognition. In a specific embodiment, antibody is initially administered during the acute phase as an intravenous infusion, intravenous or subcutaneous injection or delivered directly into the brain ventricles or intrathecally.

Administration can be prolonged and used during the inpatient neurorehabilitation to further improve recovery.

It is known that peptides, prone to aggregate after an acute brain injury event, and which in monomer, oligomer and protofibril forms are the target for the methods according to the invention, may appear in various lengths, e.g. as a result of "imperfect" cleavage reactions in connection with production or as a result of the action of various enzymes at some stage. Again with examples from the Aβ system, the full length peptide, the Aβ peptide, is in most cases 1-39, 1-40, 1-41, 1-42 and 1-43. However, truncations at one or both (N-terminal and/or C-terminal) ends of the peptides are far from uncommon, and the 1-28, 3-40/42, 11-40/42, 17-40/42 and 24-35 are just a few examples of Aβ peptides with various lengths which may appear in the in vivo system. Also, the truncated peptides can aggregate to the oligomer, protofibril and fibril forms mentioned above which means that in vivo aggregated forms of Aβ may contain various combinations and amounts of full length and truncated forms. Aggregated forms of truncated Aβ, including protofibrils, are also targets of the present methods. Antibodies against such truncated protofibrils are disclosed in WO 05/123775 and WO 2011/001366, which are hereby incorporated by reference in their entirety, and are suitable for use in the present methods.

Further variants of the peptides, prone to aggregate, may comprise mutated forms, where one or more of the amino acids in the peptide sequence are exchanged for a different amino acid. The Flemish (A21G), Arctic (E22G), Dutch (E22Q), Italian (E22K) and Iowa (D23N) mutations are well known and characterized. In particular, the Arctic mutation has been found to be of interest with regard to aggregation as it easily forms fairly stable and toxic Aβ protofibrils. Antibodies against aggregated forms of such mutants, including protofibrils thereof, are also suitable for use in the present methods.

Another peptide in the brain is α-synuclein which also aggregates under certain conditions to give various oligomer forms, protofibrils and fibrils. This peptide and its aggregated forms are strongly linked to the development of Parkinson's disease and Dementia with Lewy bodies. As in the Aβ case, efforts have been focused on the development of therapies targeting the various α-synuclein aggregated species. Several antibodies targeting the α-synuclein protofibrils are disclosed in WO 2011/104696, which is hereby incorporated by reference in its entirety, and are also suitable for use in the present methods.

According to one aspect of the invention, a method is provided wherein a person suffering from, or suspected to be a victim of an acute brain injury event, is treated with an agent targeting one or more of these peptides and/or aggregates already formed from such peptides. In specific embodiments, soluble and/or insoluble aggregated forms are targeted. The agent is administered to exert its effect in the brain and must penetrate the blood brain barrier if administered systemically. A possible administration is directly into the brain parenchyma.

In a specific embodiment of the invention, the agent is an antibody targeting protofibrils. In a more specific embodiment of the invention, the agent is an antibody targeting Aβ protofibrils. An example of a suitable drug candidate is a humanized antibody based on mAb158, disclosed in WO 07/108756, which provides a detailed disclosure of the antibody and is incorporated herein by reference in its entirety.

An antibody targeting peptides prone to aggregate and/or one or more aggregated forms thereof should have high affinity for one or more of these species. In specific embodiments, the antibody has high affinity for one or more protofibril(s). High affinity is defined as an ELISA method IC50 (the concentration of antibody needed to inhibit 50% of the assay signal) of less than $10^{-7}$ M, less than $10^{-8}$ M, less than $10^{-9}$ M, less than $10^{-10}$ M, or assay $10^{-11}$ M. In a more specific embodiment, in addition to the high affinity for one or more of the peptide species, the antibodies are of IgG class, e.g. IgG1 or IgG4 subclass or combinations or mutations thereof, and in a more specific embodiment, in addition retain high Fc receptor binding and low C1 (C1q) binding, effective in clearance of the targeted peptide specie(s) and with reduced risk of inflammation.

In one embodiment of the method for treatment of traumatic brain injury in an individual, which comprises administering to the individual a therapeutically effective and physiologically acceptable amount of an agent reducing in the brain of an individual the amount of one or more aggregated forms of a peptide, prone to aggregate as a result of a traumatic brain injury event, the amount of aggregates is reduced at least by 30%, 40%, 50%, 60%, 70%, 80% or 90% compared to a control. Even as low as 1% reduction may have significant clinical benefits.

It is believed that the time range from the traumatic brain injury event to treatment in accordance with the invention should be as short as possible. This means that a patient reaching the emergency unit of a hospital with a suspected traumatic brain injury should be treated immediately in accordance with the present invention, and at least for a period in which increased levels of peptide aggregates caused by the traumatic brain injury event are present.

It is believed that increased levels of soluble Aβ protofibrils in the brain will after many years cause dementia, in particular, Alzheimer's disease. For this reason, this invention also pertains to a chronic/preventive treatment of TBI with an agent reducing neurodegeneration which may cause dementia and Alzheimer's disease. For example, an individual at risk of later complications from TBI can be the subject of preventive treatment.

The formation of aggregates as a result of the brain injury event is of course of diagnostic or perhaps more correctly predictive value, alone or in combination with traditional characteristics of a brain disease of this type. The formation of aggregates of this type in the brain after a traumatic brain injury event indicates a risk for severe complications. For diagnosis/predication of risk, labeled substances targeting one or more of the peptide aggregates, for example, a labeled antibody, can be injected and the localization and amount of aggregates can be measured, e.g. by PET or MRI techniques. For example, fluorescent, magnetic, or radio-labeled antibodies may be employed. Alternatively, tissue of body fluid samples can be collected for in vitro analysis. In particular, antibodies against one or more of the aggregated forms, e.g., the protofibrils, are of great importance in such methods.

In one aspect of the invention there is provided a method of preventing, alleviating or treating traumatic brain injury in an individual, comprising administering to the individual a therapeutically effective and physiologically acceptable amount of an agent capable of reducing the amount of one or more aggregated forms of one or more peptides in the brain of the individual.

In one embodiment of this aspect, the traumatic brain injury is a result of an acute brain injury event. In one embodiment of this aspect, the traumatic brain injury is a result of physical brain injury event. In one embodiment of this aspect, the traumatic brain injury is a result of brain injury caused by stroke or hypoxia.

In one embodiment of this aspect, the one or more peptides are selected from the group consisting of Aβ peptides, alpha-synuclein peptides and tau-peptides.

In one embodiment of this aspect, the one or more aggregated forms of peptides are aggregated Aβ peptides in the form of protofibrils.

In one embodiment of this aspect, the agent is an antibody. In a specific embodiment, the antibody binds Aβ protofibrils.

In one embodiment of this aspect, the traumatic brain injury is mild traumatic brain injury. In one embodiment of this aspect, the traumatic brain injury is medium traumatic brain injury. In one embodiment of this aspect, the traumatic brain injury is severe traumatic brain injury.

In one embodiment of this aspect, the individual is a carrier of an Apolipoprotein E4 allele. In one embodiment of this aspect, the individual is of Apolipoprotein E3/E4 or Apolipoprotein E4/E4 genotype.

In one aspect of the invention there is provided an agent capable of reducing the amount of one or more aggregated forms of one or more peptides, in the brain, for use in preventing, alleviating or treating traumatic brain injury. In a specific embodiment, the agent is a medicament for use in preventing, alleviating or treating traumatic brain injury.

In one embodiment of this aspect, the traumatic brain injury is a result of an acute brain injury event. In one embodiment of this aspect, the traumatic brain injury is a result of physical brain injury event. In one embodiment of this aspect, the traumatic brain injury is a result of brain injury caused by stroke or hypoxia.

In one embodiment of this aspect, the one or more peptides are selected from the group consisting of Aβ peptide, alpha-synuclein peptide and tau-peptides.

In one embodiment of this aspect, the one or more aggregated forms of peptides are aggregated Aβ peptides in the form of protofibrils.

In one embodiment of this aspect, the agent is an antibody. In a specific embodiment, the antibody binds Aβ protofibrils.

In one embodiment of this aspect, said traumatic brain injury is mild traumatic brain injury. In one embodiment of this aspect, said traumatic brain injury is medium traumatic brain injury. In one embodiment of this aspect, said traumatic brain injury is severe traumatic brain injury.

In one embodiment of this aspect, said agent for use is for an individual being a carrier of an Apolipoprotein E4 allele.

In one embodiment of this aspect, said agent for use is for an individual being of Apolipoprotein E3/E4 or Apolipoprotein E4/E4 genotype.

In one aspect of the invention there is provided a method for predication of the risk for complications after a traumatic brain injury in an individual, comprising detecting one or more aggregated forms of one or more peptides prone to aggregate as a result of a traumatic brain injury event, in the brain of the individual, wherein an increased level of such one or more aggregates in the brain indicates an increased risk for complications.

In one embodiment of this aspect, the one or more peptides are selected from the group consisting of Aβ peptides, alpha-synuclein peptides and tau-peptides.

In one embodiment of this aspect, the one or more aggregated forms of peptides are aggregated Aβ peptides in the form of protofibrils.

In one embodiment of this aspect, the one or more aggregated forms of peptides are detectable with an antibody.

In one embodiment of this aspect, the one or more aggregated forms of peptides are detectable with an antibody that binds Aβ protofibrils.

In one embodiment of this aspect, the method further comprises determination of Apolipoprotein genotype.

The following non limiting example illustrates certain aspects of the invention.

EXAMPLE 1

The use of human post mortem brain material was approved by the regional ethical committee in Uppsala (decision number 2009/089). Written informed consent was obtained from all subjects involved in the study (or their relatives).

This Example studied twelve severe TBI subjects. Five post-mortem AD temporal cortex brain samples (AD1 (Swedish mutation carrier), AD3, AD10, AD13, and AD18), and four neurologically intact (NI) control samples (UBB12, UBB23, UBB24 and UBB31) from Uppsala brain bank, and patients with normal pressure hydrocephalus (NPH) (n=4), were also included in this study. Characteristics of the twelve severe TBI subjects are provided in Table 1 below:

TABLE 1

| Patient # | Age | Gender | Cause of injury | Other injuries | time post-injury (h) | Region of surgery | Surgery | GMS pre-op | Histology |
|---|---|---|---|---|---|---|---|---|---|
| #1 | 22 | M | MVA | Thi | 9 | LT | Ccx + DC | 4 | — |
| #2 | 72 | M | Fall | None | 4 | LF | Ccx + DC | 2 | — |
| #3 | 40 | M | MVA | None | 4 | RF | Ccx | 5 | — |
| #6 | 74 | M | Fall | None | 4 | RT | Ccx | 5 | Aβ, AA |
| #7 | 58 | M | Fall | Efx | 9 | LT | Ccx | 5 | No Aβ |
| #8 | 49 | M | Fall | None | 84 | RT | Ccx* | 5 | No Aβ |
| #9 | 19 | F | Fall | None | 16 | RFT | Ccx + DC^^ | 3 | No Aβ |
| #10 | 65 | M | Fall | Ffx, Thi | 180 | LT | Ccx | 3 | Aβ |
| #11 | 25 | M | SPR | None | 24 | LFP | Ccx + DC** | 2 | APP, AS |
| #14 | 67 | M | HBO | None | 4 | LT | Ccx | 5 | Aβ, AA |
| #15 | 51 | M | Fall | None | 53 | RF | Ccx + DC | 5 | No Aβ |
| #16 | 52 | M | Fall | None | 42 | RT | Ccx*** | 4 | No Aβ |

*coagulopathy

^^DC prior to Ccx, performed at re-surgery

**Initial surgery for aSDH and DC in primary hospital, CCX + revised DC secondary surgery

***Initial surgery for aSDH, Ccx at re-surgery

Abbreviations:

DC = Decompressive craniectomy, M = male; F = female; L = left; R = right; T = temporal; F = frontal, P = parietal, Ccx = removal of cortical contusion; GMS = motor component of the Glasgow Coma Scale; SPR = sports-related; MVA = motor-vehicle accident; HBO = hit by object; Thi = thoracic injury; Efx = extremity fracture; Ffx = facial fracture, GOS = Glasgow Outcome Scale; Aβ = beta-amyloid, AA = amyloid angiopathy; APP = amyloid precursor protein; AS = axonal swelling.

Methods

The biopsies and brain samples were homogenized on ice using Dounce homogenizer (2×10 strokes) in 1:10 weight: volume Tris buffered saline (20 mM Tris, 137 mM NaCl) with the addition of protease inhibitors, according to the manufacturer (Complete Mini, Roche). The samples were centrifuged at 16000×g for 1 h at +4° C. and the supernatants were defined as TBS extracts.

Aβ 1-42 peptides were purchased from American Peptide Company, Calif., USA (batch #12077006T). Lyophilized peptides were dissolved to 100 μM in 10 mM NaOH. Aβ 1-42 protofibrils were prepared by diluting the Aβ 1-42 peptide to 50 μM in 0.1 M Phosphate buffer containing 0.3 M NaCl, pH 7.4. The preparation was incubated for 30 min at 37° C. and then centrifuged at 16000×g for 5 min to pellet potential large aggregates. The supernatants were further purified from monomers by size exclusion chromatography (Superdex 75 column, GE Healthcare, Sweden) at a flow rate of 0.08 ml/min in 0.05M Phosphate buffer, 0.15M NaCl, pH 7.4, and protofibrils were collected in the void fraction as previously described (Nilsberth C et al., (2001) Nat Neurosci 4, 887-893; Walsh D M et al., (1997) J Biol Chem 272, 22364-22372; Sehlin D et al., (2012) PloS One 7, e32014).

A conventional assay for determination of total protein content was used to generate a dataset for normalization of Aβ-data (BCA protein assay kit, #23227, Pierce).

*Assay for Aβ Protofibrils*

The mAb158 sandwich ELISA, previously described in Englund H et al. (2007 J Neurochem 103, 334-345), specifically detects Aβ protofibrils without interference from Aβ monomers. The protofibril-selective monoclonal mouse antibody mAb158 (IgG2a, BioArctic Neuroscience, Stockholm, Sweden) was formulated in sterile PBS (pH 7.5) at a concentration of 2 mg/ml and has previously been characterized. ELISA plates were coated with 2 μg/ml mAb158 in PBS overnight at +4° C. and blocked with 1% BSA in PBS for 1 h. TBS extracts were diluted fivefold and incubated in duplicates for 2 h at 22° C. with shaking (600 rpm), thereafter biotinylated mAb158 (0.5 μg/ml) was added and the plates were incubated for another hour. Streptavidin-HRP (Mabtech, Sweden 1: 5000) was used as detection agent (1 h incubation). Plates were developed with TMB substrate and the reaction was stopped after 25 min by the addition of 2M $H_2SO_4$. Optical density was measured at 450 nm and sample concentrations were calculated from an Aβ42 protofibril standard curve using a 4-parameter equation. Data was re-calculated together with the total protein dataset and presented as pg protofibril per mg total protein in each sample.

Assay for Aβ Oligomers/Protofibrils (OLs)

The mAb82E1 sandwich ELISA detects Aβ oligomers/protofibrils (dimers to protofibrils) without binding Aβ monomers (Tucker S et al., (2015) J Alzheimer's Dis. 2015; 43(2):575-88, Supplementary FIG. 4). mAb82E1 is an antibody that detects the N-terminus of β-secretase cleaved AβPP (IBL, Japan). In the mAb82E1 sandwich ELISA described here, pure mAb82E1 is used for capture and the same biotinylated antibody for detection. The sandwich ELISA protocol for mAb82E1 was in essence the same as for mAb158 sandwich ELISA above, with the exceptions that both coating of the ELISA plate and detection was carried out at a mAb82E1 concentration of 0.25 μg/ml. Sample concentrations were calculated from an Aβ 42 protofibril standard curve using a 4-parameter equation. Data was re-calculated together with the total protein dataset and presented as pg oligomer per mg total protein in each sample.

Monomeric Aβ 38, 40 and 42

Two different immunoassay kits measuring both full-length and truncated forms (mAb6E10 detection, cat no. K15200E-2 and mAb4G8 detection, cat no. K15199E-2) of Aβ 38, Aβ 40 and Aβ42 in a three-in-one (triplex) well format, were obtained from Meso Scale Discovery (Rockville, Md., USA). TBS extracts were subject to denaturation and monomerisation by boiling in 1% SDS prior to 10-fold dilution and addition to duplicate wells. The same final concentration of SDS (0.1%) was added to the Aβ standards supplied with the kits, and this procedure has been shown not to interfere with the assay (data not shown). Data was re-calculated and presented as pg Aβ per mg total protein in each sample.

HAMA Analysis

Human Anti-Mouse Antibodies (HAMA) are found in 10-20% of naive serum samples and can potentially cross-link the antibodies in a sandwich ELISA method, resulting in false positive signals (Koshida et al., 2010). In order to address HAMA, the mAb158 and mAb82E1 ELISAs were run in the presence of HAMA buffer (365 J2, Mabtech, Sweden) and with coating of the ELISA plate with irrelevant mouse IgG (015-000-003, Jackson Immuno Research, West Grove, Pa., USA).

Apolipoprotein E Genotyping

Apolipoprotein E (ApoE) genotyping was performed essentially as described in Hixson and Vernier (J Lipid Res 1990, March; 31(3):545-8) with slight modification of the primer sequences. Genomic DNA was prepared from 25 mg brain tissue using a commercial kit (QIAamp DNA Mini Kit, cat no 51304). 40 ng DNA was PCR amplified using Taq polymerase as described by the manufacturer (Thermo Scientific, cat no AB0908) using forward ApoE primer (AGACGCGGGCACGGCTGTCCAAGGAGC) (SEQ ID NO: 1) and reverse ApoE primer (TCGCGGGCCCCGGCCTGGTACACTGC) (SEQ ID NO: 2) with the addition of 5% DMSO. The PCR cycling completed 35 rounds of: denaturation 95° C.—1 min, annealing, 95° C.—1 min and elongation 72° C.—1.5 min. The 244 bp PCR product was cleaved using the restriction enzyme Hha I according to the manufacturer (Thermo Scientific, cat no. 10819870) and the digested fragments were separated on a high resolution 4% MetaPhor™ agarose gel (Lonza, cat no 50181).

Results

Traumatic brain injury (TBI) is an established risk factor of Alzheimer's disease (AD). A hallmark pathological finding in AD brains is insoluble plaques of amyloid-beta (Aβ) although recent evidence suggests that soluble and neurotoxic Aβ oligomers (OLs) and protofibrils (PFs) may be more important causes of cognitive impairment and neurodegeneration. Surprisingly, Aβ plaques were previously observed within hours in a subset of TBI patients, persisting up to several years after severe TBI. However, the role for the potentially neurotoxic Aβ OLs and PFs in TBI has not been established.

Enzyme-linked immunosorbent assay (ELISA) was used to evaluate the presence of Aβ oligomers and protofibrils (OLs) in brain tissue, surgically resected during the first post-injury week in the described 12 severe TBI patients (mean 49.6 years, range 19-74) due to life threatening brain swelling and/or intracranial pressure elevations. Post-mortem brain tissue from the AD patients (n=5), and cortical biopsies from patients with normal pressure hydrocephalus (n=4) and post-mortem brain tissue from neurologically intact (NI) patients dying from unrelated causes (n=4) were used as controls. Immunohistochemistry of a subset of the TBI tissue (n=9) revealed Aβ plaques in 3/9 TBI patients. Aβ OLs (median 129 (range 29-342) vs. 0 (range 0-0) pg/mg total protein, $p<0.01$) and PFs (median 17.5 (range 0-626) vs. 0 (range 0-0) pg/mg total protein, $p<0.01$) levels were increased in TBI patients when compared to the control group. The levels of Aβ OLs and PFs in brain tissue were also higher in TBI (median OLs 129, range 29-342 and PFs 17.5, range 0-626 pg/mg total protein) in comparison with AD patients (median OLs 27, range 0-399, p=0.16 and PFs 0, range 0-78, p=0.37). Patients with immunohistochemical evidence of Aβ plaques had the highest levels of Aβ PFs. We conclude that human TBI induces rapid accumulation of soluble Aβ oligomers and protofibrils in injured brain tissue. Induction of soluble Aβ species may aggravate the secondary brain injury and contribute to the increased risk of AD after TBI.

Results from the ApoE genotyping are provided in the Table 2 below.

TABLE 2

| Patient # | ApoE Genotype |
|---|---|
| #1 | E3/E3 |
| #2 | E3/E3 |
| #3 | E3/E3 |
| #6 | E3/E4 |
| #7 | E3/E3 |
| #8 | E3/E4 |
| #9 | E2/E4 |
| #10 | E3/E4 |
| #11 | E3/E3 |
| #14 | E3/E4 |
| #15 | E3/E3 |
| #16 | E3/E3 |

The PCR amplification and Hha I restriction was performed in three separate experiments with similar results. Four out of 12 TBI patients with high Aβ protofibril levels (FIG. 1A) were identified as being of E3/E4 genotype. Of the remaining 8 patients, 7 patients with low or undetectable Aβ protofibril levels are of E3/E3 genotype and 1 patients with low or undetectable Aβ protofibril levels is of E2/E4 genotype.

The E3/E4 genotype is the most common genotype in the AD group and among the Hydrocephalus controls 1 out of 4 patients carry the E3/E4 genotype, a frequency similar to what is expected in the general population (http://www.alzgene.org/meta.asp?gene)D=83).

The data suggest a link between carrying the E3/E4 genotype and responding with high Aβ protofibril levels shortly after a traumatic brain injury.

Results from running the mAb158 and mAb82E1 ELISAs with standard settings in parallel with HAMA buffer and/or irrelevant mouse IgG coating suggested that the observations were true and not a consequence of HAMA activity in the assays (data not shown). It was concluded from the study that in 4 out of 12 TBI patients (33%), it was possible to measure elevated Aβ protofibril levels as compared to control brains. In the same 4 TBI patients, elevated levels of soluble Aβ42 levels were detected as compared to control brains. In 11 out of 12 TBI patients, elevated Aβ oligomer levels were measured as compared to control brains. The soluble Aβ42 are pre-dominantly N-terminally truncated forms.

The specific examples and embodiments described herein are exemplary only in nature and are not intended to be limiting of the invention defined by the claims. Further embodiments and examples, and advantages thereof, will be apparent to one of ordinary skill in the art in view of this specification and are within the scope of the claimed invention.

The invention claimed is:

1. A method of alleviating or treating traumatic brain injury in an individual, comprising administering to the individual a therapeutically effective and physiologically acceptable amount of an antibody which binds Aβ protofibrils, wherein said antibody is mAb158 or a humanized version thereof.

2. The method of claim 1, wherein said traumatic brain injury is a result of an acute brain injury event.

3. The method of claim 1, wherein said traumatic brain injury is a result of physical brain injury event.

4. The method of claim 1, wherein said traumatic brain injury is a result of brain injury caused by stroke or hypoxia.

5. The method according to claim 1, wherein said traumatic brain injury is mild traumatic brain injury.

6. The method according to claim 1, wherein said traumatic brain injury is moderate traumatic brain injury.

7. The method according to claim 1, wherein said traumatic brain injury is severe traumatic brain injury.

8. The method according to claim 1, wherein said individual has been determined to be a carrier of an Apolipoprotein E4 allele as determined by genotyping.

9. The method according to claim 1, wherein said individual has been determined to be of Apolipoprotein E3/E4 or Apolipoprotein E4/E4 genotype.

10. A method of binding an amount of Aβ protofibrils in the brain of an individual having a traumatic brain injury, comprising administering to the individual a physiologically acceptable amount of an antibody which binds Aβ protofibrils, wherein the antibody is mAb158 or a humanized version thereof, wherein the antibody is labelled with a detectable label, and measuring the localization and amount of the aggregated AP peptide binding with the labelled antibody.

11. Method according to claim 10, wherein the antibody is fluorescent, magnetic, or radio labelled.

* * * * *

UNITED STATES PATENT AND TRADEMARK OFFICE

CERTIFICATE OF CORRECTION

PATENT NO. : 11,327,080 B2
APPLICATION NO. : 15/746283
DATED : May 10, 2022
INVENTOR(S) : Lars Lannfelt et al.

It is certified that error appears in the above-identified patent and that said Letters Patent is hereby corrected as shown below:

On the Title Page

At item (73), Line 1, “BioArctic Neruoscience AB” should be -- BioArctic AB --.

Signed and Sealed this
Twenty-second Day of November, 2022

Katherine Kelly Vidal

Katherine Kelly Vidal
*Director of the United States Patent and Trademark Office*

SEQUENCE LISTING

```
<160> NUMBER OF SEQ ID NOS: 2

<210> SEQ ID NO 1
<211> LENGTH: 27
<212> TYPE: DNA
<213> ORGANISM: Artificial Sequence
<220> FEATURE:
<223> OTHER INFORMATION: Primer

<400> SEQUENCE: 1

agacgcgggc acggctgtcc aaggagc                                          27


<210> SEQ ID NO 2
<211> LENGTH: 26
<212> TYPE: DNA
<213> ORGANISM: Artificial Sequence
<220> FEATURE:
<223> OTHER INFORMATION: Primer

<400> SEQUENCE: 2

tcgcgggccc cggcctggta cactgc                                           26
```